United States Patent
Grosse

(10) Patent No.: US 7,396,158 B2
(45) Date of Patent: Jul. 8, 2008

(54) MOBILE FLAT X-RAY DETECTOR HAVING A CARRY GRIP

(75) Inventor: Burkhard Grosse, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/405,442

(22) Filed: Apr. 18, 2006

(65) Prior Publication Data

US 2006/0256928 A1    Nov. 16, 2006

(30) Foreign Application Priority Data

Apr. 18, 2005    (DE) .................... 10 2005 018 004

(51) Int. Cl.
*H01J 31/49*    (2006.01)
*G01B 15/02*    (2006.01)

(52) U.S. Cl. ..................... 378/189; 378/98.8
(58) Field of Classification Search ............... 378/19, 378/22, 98.8, 167–169, 182, 189; 250/370.09
See application file for complete search history.

(56) References Cited

U.S. PATENT DOCUMENTS

| | | | |
|---|---|---|---|
| 5,090,047 A * | 2/1992 | Angotti et al. ............... 378/170 |
| 5,539,799 A | 7/1996 | Schulze-Ganzlin et al. |
| 5,661,309 A * | 8/1997 | Jeromin et al. ............... 250/580 |
| 6,296,386 B1* | 10/2001 | Heidsieck et al. ........... 378/189 |
| 6,855,936 B2* | 2/2005 | Yamamoto ............. 250/370.09 |
| 6,899,459 B1* | 5/2005 | McKenna ................... 378/181 |
| 6,966,695 B2* | 11/2005 | Boomgaarden et al. ..... 378/177 |
| 7,092,491 B2* | 8/2006 | Okoda ........................ 378/162 |
| 2002/0150214 A1 | 10/2002 | Spahn |
| 2002/0181659 A1* | 12/2002 | Watanabe et al. ........... 378/189 |
| 2003/0091156 A1* | 5/2003 | Crain et al. ................. 378/197 |
| 2004/0120460 A1 | 6/2004 | Kuramoto et al. |
| 2006/0034427 A1* | 2/2006 | Brooks ....................... 378/198 |
| 2006/0113481 A1* | 6/2006 | Murphy et al. ......... 250/370.09 |

FOREIGN PATENT DOCUMENTS

DE    42 38 268 C 2    5/1994
EP    1 262 821 A1    12/2002

OTHER PUBLICATIONS

Sirona: "SIDEXIS-Intraoral sensors", www.sirona.com/ecomaXL/index.php.
German Office Action dated Jan. 31, 2006.

* cited by examiner

*Primary Examiner*—Irakli Kikandze
(74) *Attorney, Agent, or Firm*—Harness, Dickey & Pierce, P.L.C.

(57) ABSTRACT

A mobile flat X-ray detector is for an X-ray diagnostic device. The detector includes an X-ray detector, a detector housing and a carry grip attached on a longitudinal side of the detector housing. The detector housing is provided on at least one further side with a receptacle for a carry grip and/or handle.

20 Claims, 2 Drawing Sheets

MOBILE FLAT X-RAY DETECTOR HAVING A CARRY GRIP

The present application hereby claims priority under 35 U.S.C. §119 on German patent application number DE 10 2005 018 004.3 filed Apr. 18, 2005, the entire contents of which is hereby incorporated herein by reference.

FIELD

The invention generally relates to a mobile flat X-ray detector for an X-ray diagnostic device. For example, it may relate to one including a detector housing and a carry grip attached on a longitudinal side of the detector housing.

BACKGROUND

US 2002/0150214 A1 discloses an X-ray device having a transportable radiation receiver that can be inserted into a drawer below a patient support table, or can be placed on the patient support table below the patient. For the purpose of transport and of better placement, such a flat X-ray detector usually has on its longitudinal side a carry grip that can be exchangeable. Such a flat X-ray detector having a grip is known, for example, from the brochure by Siemens Medical Solutions entitled "AXIOM Multix M Your portal to the world of direct digital radiography" with order number A91100-M1200-B527-2-7600.

The flat X-ray detectors can be used both for free imaging and for pulmonary images with the aid of a mobile X-ray diagnostic device in bed, so-called bed lungs.

Particularly in the case of bed lungs, but also with other applications, the detector is placed completely below the patient. In this case, the patient likewise lies completely on the carry grip, since the latter is attached on the longitudinal side of the flat X-ray detector, which lies transverse to the bed. Above all else, it is difficult with patients who are older, traumatized or otherwise difficult to move for handling to be carried out below the patient, to place the flat X-ray detector and to remove it.

SUMMARY

An object of at least one embodiment includes designing a transportable flat X-ray detector in such a way that the flat X-ray detector can be operated more easily particularly in the case of bed-bound images.

An object according to at least one embodiment of the invention may be achieved by virtue of the fact that the detector housing is provided on at least one further side with a receptacle for a grip.

The flat X-ray detector can also further be easily placed when an additional handle can be inserted in a latching fashion into one of the further side receptacles.

According to at least one embodiment of the invention, the carry grip may be removeably attached on the detector housing by way of receptacles. Here, it is possible to achieve any desired attachment of the carry grip when it can be removeably inserted into one of the further receptacles in a latching fashion by way of a detachable connection.

It is advantageously possible for a cable connection to be attached to the grip, the cable connection being able to have a data line and/or a line for supplying power.

BRIEF DESCRIPTION OF THE DRAWINGS

The invention is explained below in more detail with the aid of example embodiments illustrated in the drawings, in which.

DETAILED DESCRIPTION OF THE EXAMPLE EMBODIMENTS

Figure 1:
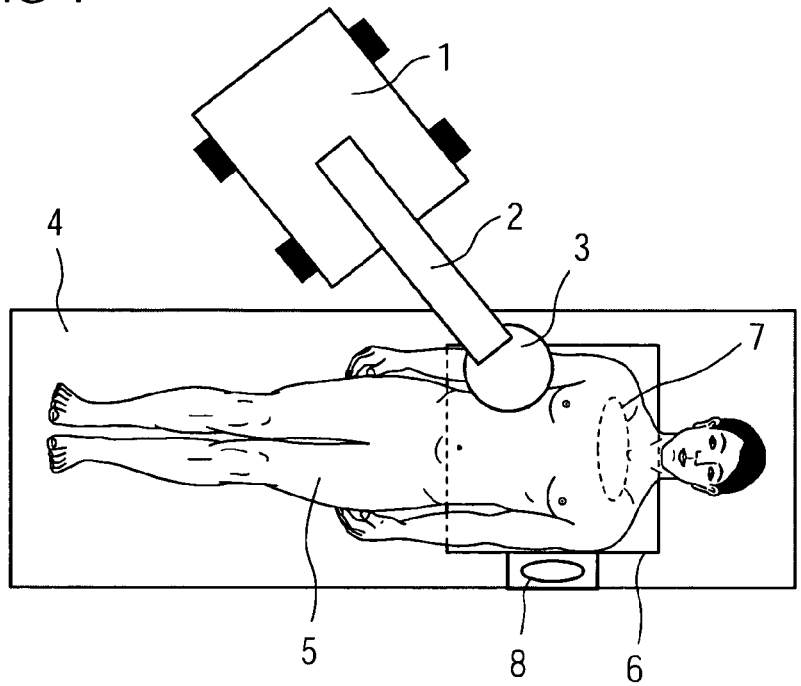
FIG. 1 shows a schematic of a mobile X-ray diagnostic device having a mobile flat X-ray detector according to at least one embodiment of the invention.

FIG. 1 is a schematic of a mobile X-ray diagnostic device having an X-ray generator 1 on which an X-ray emitter 3 is attached via a support arm 2. A patient 5 lying in a bed or on a patient support table 4 is intended to be transirradiated.

Arranged below the patient 5 is a mobile flat X-ray detector 6. On its long side, the latter has a carry grip 7 by means of which it can be carried and can be placed for taking an image, for example a bed lung. However, the patient 5 lies fully on the carry grip 7, and so the latter cannot be grasped at all or only with difficulty. For this reason, there is provided according to the invention a handle 8 that can be fastened on the short side of the flat X-ray detector 6 so that it can be more effectively grasped for positioning.

Figure 2:
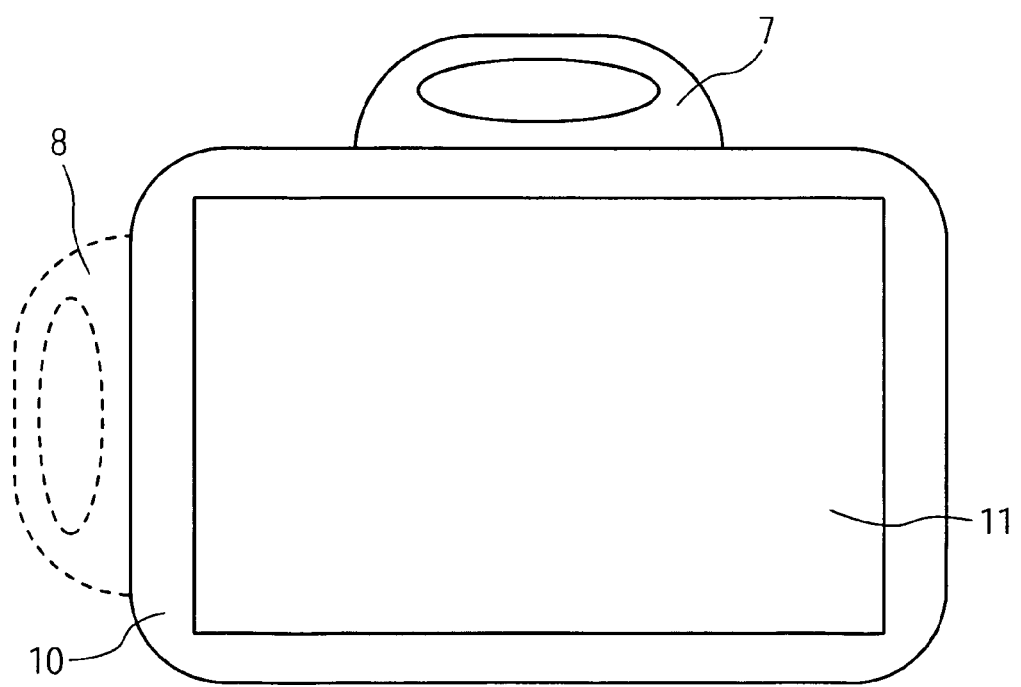
FIG. 2 shows a flat X-ray detector according to at least one embodiment of the invention.

FIG. 2 illustrates such a flat X-ray detector 6 that has a detector housing 10 with a detector 11 lying inside. The carry grip 7, which can be connected permanently to the detector housing 10, is attached on the longitudinal side. However, it can also be removable. The handle 8 can be attached on the other side as will be described in the text which follows.

Figure 3:
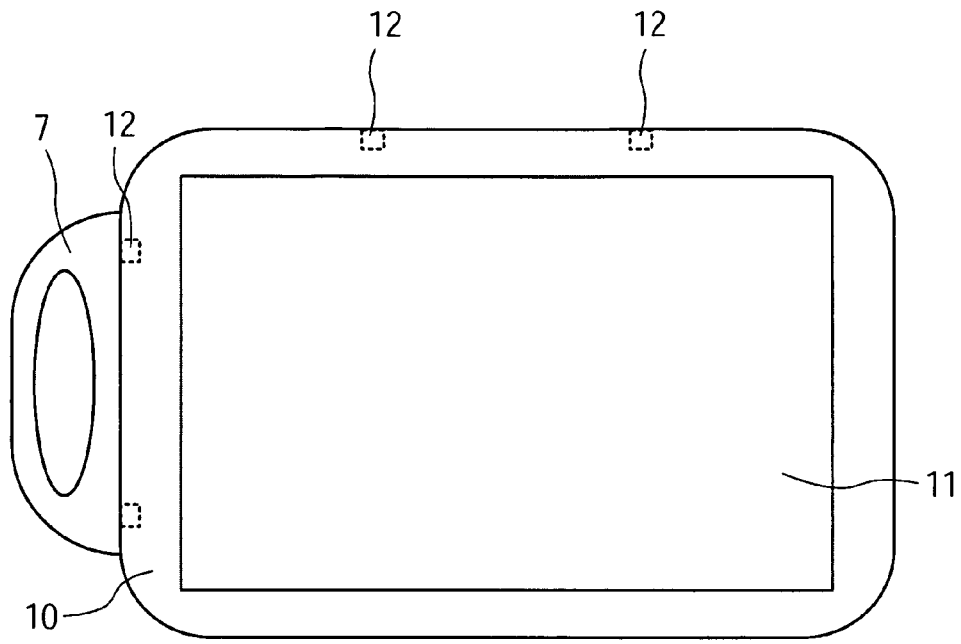
FIG. 3 shows a second embodiment of a flat X-ray detector according to at least one embodiment of the invention.

However, it is also possible in the case of a removable carry grip 7 for the latter to be repositioned to the narrow side, as is illustrated in FIG. 3. In this case, pins 13, for example, can engage in receptacles 12 for the purpose of stabilization.

Figure 4:
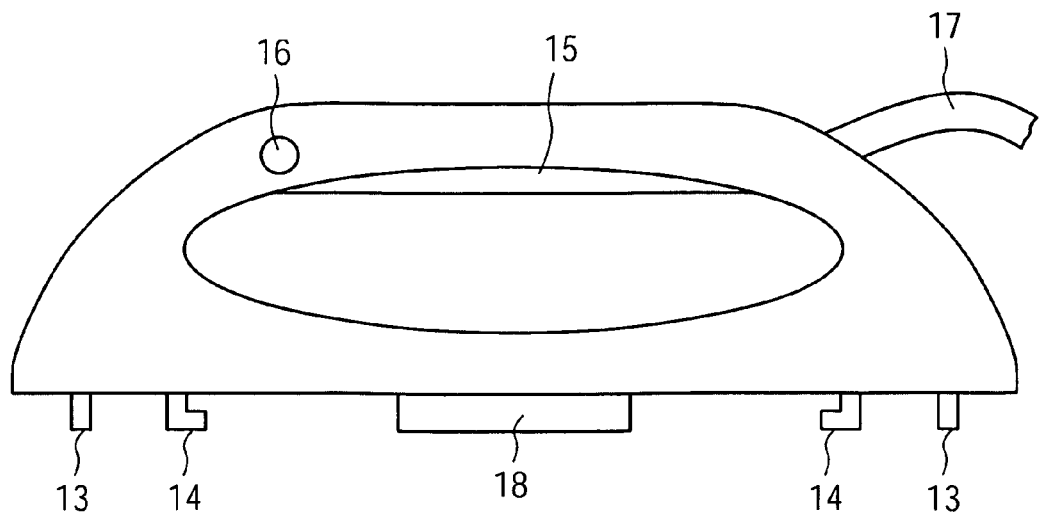
FIG. 4 shows a detailed view of a detachable handle.

For the purpose of fastening the carry grips 7 and handles 8 securely on the detector housing 10, these can be provided with a locking mechanism reproduced in FIG. 4, whose locking hooks 14 which point in opposite directions are inserted into openings (not illustrated) in the detector housing 10 and engage the housing wall from behind. So that the locking hooks 14 can be inserted into the detector housing 10, an unlocking grip 15 is provided that effects spreading of the two locking hooks 14 in a known way by means of a mechanism (not illustrated) such that said unlocking hooks can be inserted into the openings provided for the purpose in the detector housing 10. Releasing the unlocking grip 15 causes the locking hooks 14 to draw together because of a spring action, and to grip the detector housing 10 from behind.

A locking button 16 that locks the unlocking grip 15 is provided so that the grips 7 or 8 are not inadvertently unlocked during transport of the flat detector 6. Thus, the first step in changing the carry grip 7 or handle 8 is to actuate the locking button 16, after which the unlocking grip 15 thus rendered free can be pressed.

Illustrated in addition in FIG. 4 is a cable connection 17 for the carry grip 7 or handle 8. This cable connection 17 can include a data line and a voltage cable such that when the carry grip 7 or handle 8 of the mobile flat X-ray detector 6 is fastened in accordance with FIG. 4 reading the data directly can be performed in addition to supplying voltage directly via the voltage network. The grip 7 or 8 then has a plug-in connection 18 with the detector housing 10 by which it is possible to supply the detector 11 with voltage and to read out the data via the cable connection 17.

The design according to at least one embodiment of the invention yields a transportable flat X-ray detector having exchangeable and/or additionally attachable carry grips or handles for simple handling, particularly in the case of bed lungs.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A mobile flat X-ray detector for an X-ray diagnostic device, comprising:
    an X-ray detector;
    a detector housing;
    a carry grip attached on a side of the detector housing, the detector housing including, on at least one further side, at least one receptacle; and
    an additional handle, insertable in a latching fashion into at least one further side receptacle.

2. The mobile flat detector as claimed in claim 1, wherein a cable connection is attached to the grip.

3. The mobile flat detector as claimed in claim 1, wherein the cable connection includes a data line.

4. The mobile flat detector as claimed in claim 1, wherein the cable connection includes a line for supplying power.

5. The mobile flat detector as claimed in claim 1, wherein the carry grip is removeably attachable via the at least one receptacle.

6. The mobile flat detector as claimed in claim 1, wherein the carry grip is removeably insertable into the at least one of the further receptacle in a latching fashion via a detachable connection.

7. The mobile flat detector as claimed in claim 1, wherein a cable connection is attached to the grip.

8. The mobile flat detector as claimed in claim 7, wherein the cable connection includes a data line.

9. The mobile flat detector as claimed in claim 7, wherein the cable connection includes a line for supplying power.

10. A mobile flat X-ray detector for an X-ray diagnostic device, comprising:
    an X-ray detector:
    a detector housing; and
    a carry grip attached on a side of the detector housing, the detector housing including, on at least one further side, at least one receptacle; wherein
    the carry grip is removeably attachable via the at least one receptacle.

11. The mobile flat detector as claimed in claim 10, wherein the carry grip is removeably insertable into the at least one of the further receptacle in a latching fashion via a detachable connection.

12. The mobile flat detector as claimed in claim 10, wherein a cable connection is attached to the grip.

13. The mobile flat detector as claimed in claim 10, wherein the cable connection includes a data line.

14. The mobile flat detector as claimed in claim 10, wherein the cable connection includes a line for supplying power.

15. The mobile flat detector as claimed in claim 10, wherein the carry grip is removeably attachable via the at least one receptacle.

16. A mobile flat X-ray detector for an X-ray diagnostic device, comprising:
    an X-ray detector;
    a detector housing; and
    a carry grip attached on a side of the detector housing, the detector housing including, on at least one further side, at least one receptacle; wherein
    the carry grip is removeably insertable into the at least one of the further receptacle in a latching fashion via a detachable connection.

17. The mobile flat detector as claimed in claim 16, wherein a cable connection is attached to the grip.

18. The mobile flat detector as claimed in claim 16, wherein the cable connection includes a data line.

19. The mobile flat detector as claimed in claim 16, wherein the cable connection includes a line for supplying power.

20. The mobile flat detector as claimed in claim 16, wherein the carry grip is removeably attachable via the at least one receptacle.

* * * * *